Jan. 21, 1964 A. MEILLAND Plant Pat. 2,349
ROSE PLANT
Filed Feb. 5, 1963 2 Sheets-Sheet 1
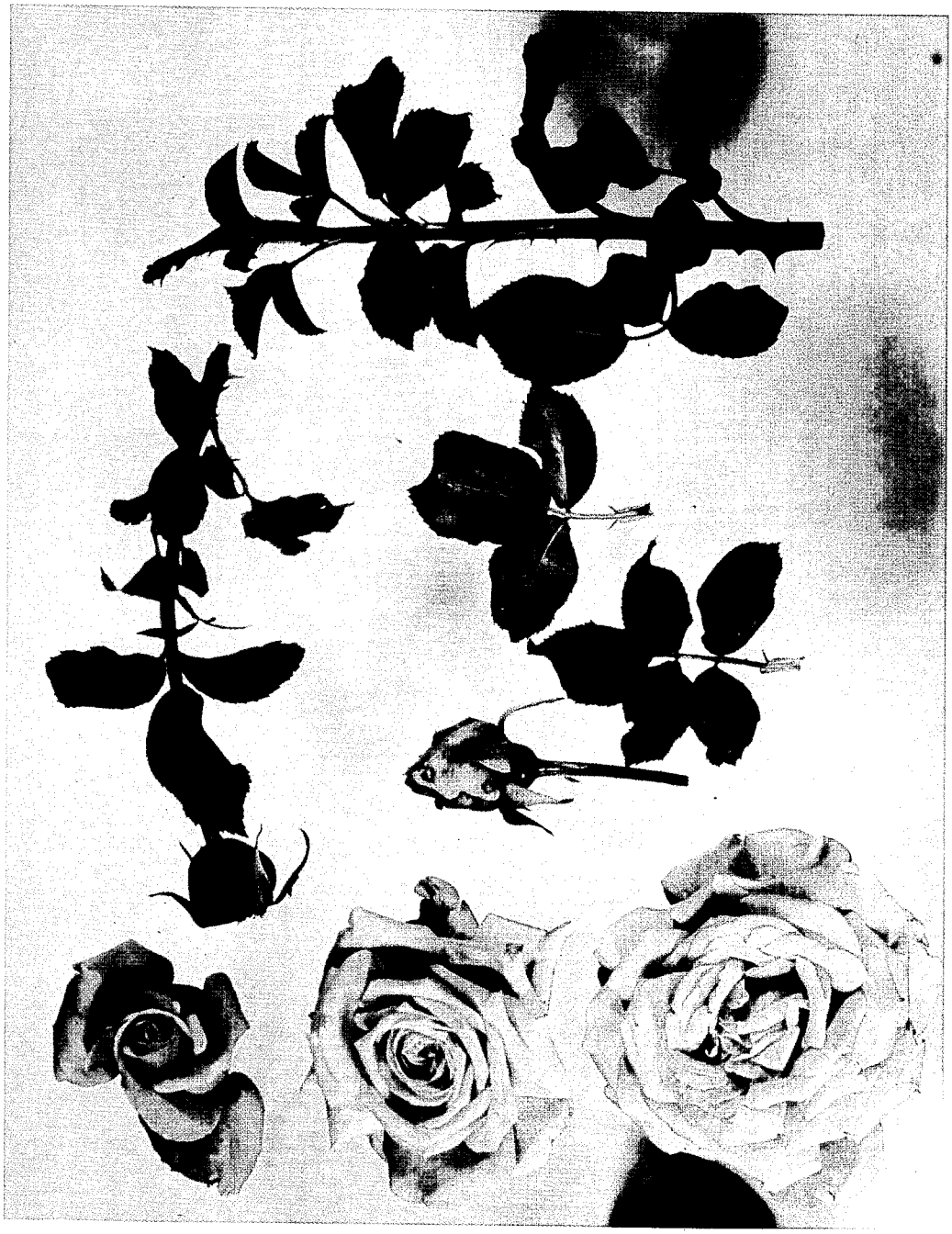
Inventor.
Alain Meilland
By: Robb & Robb
Attorneys.

Jan. 21, 1964 A. MEILLAND Plant Pat. 2,349
ROSE PLANT
Filed Feb. 5, 1963 2 Sheets-Sheet 2
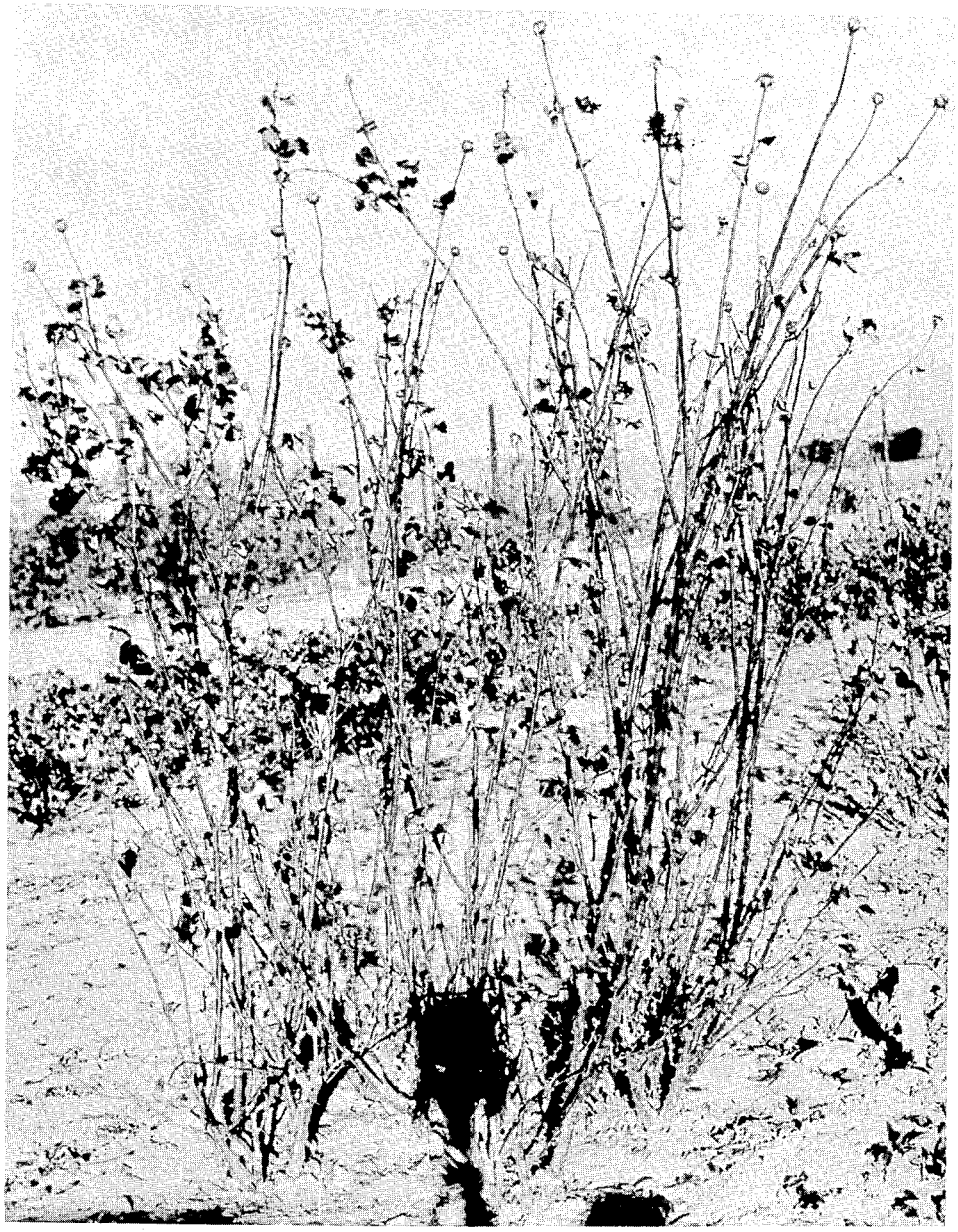
Inventor.
Alain Meilland
By: Robb & Robb
Attorneys.

United States Patent Office

Plant Pat. 2,349
Patented Jan. 21, 1964

2,349
ROSE PLANT

Alain Meilland, Alpes Maritimes, France, assignor to The Conard-Pyle Company, West Grove, Pa., a corporation of Pennsylvania

Filed Feb. 5, 1963, Ser. No. 256,486
1 Claim. (Cl. Plt.—18)

The present invention relates to a new and distinct variety of rose plant of the hybrid tea class, which was originated by me by crossing an unnamed and unpatented seedling derived from a cross of "Happiness" (U.S. Plant Patent No. 911), known in France as "Rouge Meilland," × "Independence" (U.S. Plant Patent No. 1,036), known in Germany as "Kordes' Sondermeldung," with the variety "White Knight" (U.S. Plant Patent No. 1,359), known in Europe as "Message."

The primary objective of this breeding was to produce a new rose variety having good vigor, combined with a flower and supporting structure of an improved type suitable for use for cut flowers and for garden decoration. This objective was fully achieved, as evidenced by the following unique combination of characteristics which are outstanding in the new variety and which distinguish it from its parents, as well as from all other varieties of which I am aware:

(1) Exceptional vigor, with an average plant height considerably greater than the average of other varieties grown under the same cultural conditions;

(2) Flowers of good form, with the buds being long-pointed and having the habit of opening slowly, and the flowers being of long lasting quality;

(3) A habit of bearing the flowers usually individually on stems of great length and good rigidity regardless of whether the flowers are borne singly or on cluster type main canes of candelabra form; and (4) A distinctive and attractive Neyron Rose general color tonality of the newly opened flowers, with the color changing to Tyrian Rose as the flowers age.

In comparison with the unnamed seed parent, my new variety is endowed with superior vigor and bears flowers on long stems, with the flower buds being more pointed.

As compared with its pollen parent, "White Knight," the new variety is more vigorous, has cleaner foliage, and the flowers are borne on longer stems of good cutting lengths.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawings show typical specimens of the vegative growth and flowers of my new variety in different stages of development and as depicted in color as nearly true as it is reasonably possible to make the same in a color illustration of this character, and also typical specimen plants as depicted in Black and White to illustrate the characteristic habits of plant growth and other structural features, including the flower stems.

The following is a detailed description of the new variety, with color terminology in accordance with the Horticultural Colour Chart of the Royal Horticultural Society, except where general color terms of ordinary dictionary significance are obvious:

Type: Hardy; bush; seedling; for cut flowers and for garden decoration.

Class: Hybrid tea.

Breeding: Seedling.

*Seed parent.*—An unnamed seedling derived from a cross of "Happiness" × "Independence."

*Pollen parent.*—"White Knight."

Propagation: Holds its distinguishing characteristics through succeeding propagations by budding.

*Flower*

Locality where grown and observed: West Grove, Pennsylvania, U.S.A.

Flowers Borne: Usually singly to stem, but occasionally several on candelabra-type main canes; on long and strong stems.

Quantity of bloom: Free, outdoors.

Continuity: Continuous.

Fragrance: Moderate.

*Nature.*—Tea.

Bud:

*Peduncle.*—Long; medium heavy; erect; stiff; rough; with medium number of hairs. Color—Lettuce Green, Plate 861, occasionally lightly overlaid with Garnet Brown, Plate 00918/2.

*Before calyx breaks.*—Size—medium. Form—pointed; ovoid; with a conspicuous neck; usually without foliaceous appendages on the surface of the bud; with slender bristle-like foliaceous parts extending beyond the tip of the bud equal to ¼ or more of its length.

*As calyx breaks.*—Color—Spinel Red, Plate 0023.

*As first petal opens.*—Size—medium. Form—ovoid. Color: outside—Spirea Red, Plate 025/1; inside—Neyron Rose, Plate 623/1.

*Opening.*—Opens up well.

Bloom:

*Size (when fully open).*—From 3½ to 4 inches.

*Petalage.*—Double; from 35 to 50 petals; arranged regularly.

*Form.*—Full at first but becoming cupped; petals being at first loosely rolled outward and remaining loosely rolled outward at maturity.

Petals:

*Texture.*—Medium thickness; leathery.

*Appearance.*—Inside—satiny. Outside—shiny.

*Shape.*—Outer petals—obovate. Intermediate petals—obovate. Inner petals,—undulate; irregular.

This description of a newly opened flower was made from a rose grown outdoors during the month of July at West Grove, Pennsylvania, U.S.A.

*Color.*—Outer petal—outside surface: Rose Bengal, Plate 25/2, becoming tinted with Neyron Rose, Plate 623/3 toward point of attachment, with point of attachment Uranium Green, Plate 63/3; inside surface: between Neyron Rose, Plate 623/1 and Neyron Rose, Plate 623/2, with area surrounding point of attachment near Primrose Yellow, Plate 601/3. Intermediate petal—outside surface: Rose Bengal, Plate 25/2, with point of attachment Uranium Green, Plate 63/3, and with latter color continued along midrib about ⅕ of the total length of the petal; inside surface: Between Neyron Rose, Plate 623/1 and Neyron Rose, Plate 623/2, with point of attachment near Primrose Yellow, Plate 601/3. Inner petal—outside surface: Rose Bengal, Plate 25/2, often bisected along midrib by a streak of Uranium Green, Plate 63/3 which continues down to the point of attachment; inside surface: between Neyron Rose, Plate 623/1 and Neyron Rose, Plate 623/3, often streaked along midrib with near white, and with point of attachment Primrose Yellow, Plate 601/3.

This description was made from a rose that was open for three days outdoors during the month of July at West Grove, Pennsylvania, U.S.A.

*Color.*—Outer petal—outside surface: near Magenta, Plate 27/2, becoming tinted with Magenta, Plate 27/3 over basal ¼ of petal, with point of attachment Uranium Green, Plate 63/3; inside surface: Tyrian Rose, Plate 24/3, with point of attachment Primrose Yellow, Plate 601/3. Inner petal—outside surface: near Magenta, Plate 27/2, with a streak of near white following the midrib, and with point of attachment Uranium Green, Plate 601/3; inside surface: near Tyrian Rose, Plate 24/3, margined with Tyrian Rose, Pate 24/2, and often streaked along midrib with near white, and with point of attachment Primrose Yellow, Plate 601/3.

*General color effect.*—Newly opened flower—Neyron Rose. Three days open—Tyrian Rose.

*Behavior.*—Drop off cleanly.

*Flower longevity.*—On bush in garden: 5 days in July. Cut roses grown outdoors and kept at living room temperatures: 4 days in July.

*Reproductive Organs*

Stamens: Medium number; arranged irregularly about pistils; mixed with petaloids.

Filaments: Most with anthers; from medium length to long.

*Color.*—Peony Purple, Plate 729.

Anthers: Open at various times; medium size; osccasionally an anther fused with a petaloid.

*Color.*—Yellow Ochre, Plate 07.

Pollen: Moderate quantity.

*Color.*—Gold.

Pistils: Medium number.

Styles: Uneven; medium length; medium caliper; bunched.

Stigma:

*Color.*—Yellow.

Ovaries: All enclosed in receptacle.

Hips: Globular; with inconspicuous neck; very smooth; walls medium thick and fleshy.

*Color.*—Green.

Sepals: Permanent; moderately long; straight.

Seeds: Medium number; medium size.

*Plant*

Foliage:

*Leaves.*—Compound of 3 or 5 leaflets; abundant; large; leathery.

*Leaflets.*—Shape—Roundly oval, with apex obtuse. Base—obtuse. Margin—Simply serrate.

*Color.*—Mature—Upper surface: Parsley Green, Plate 00962; under surface: Willow Green, Plate 000862, lightly overlaid with Erythrite Red, Plate 0027/1. Young—upper surface: near Purple Madder, Plate 1028, overlying Parsley Green, Plate 00962/1; under surface: near Erythrite Red, Plate 0027/1.

*Rachis (the supporting stem of the compound leaf).*—Medium size. Upper side—grooved; hairy. Under side—moderately prickly.

*Stipules.*—Moderately long; narrow; with points of medium length turning out at an angle of 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Heavy.

*Main stems.*—Dull. Color—Parsley Green, Plate 00962/2. Prickles—several, mostly straight; color: Fern Green, Plate 0862/1. Hairs—none.

*Branches.*—Dull. Color—Parsley Green, Plate 00962/2, often lightly overlaid with Garnet Brown, Plate 00918/3. Prickles—several, sometimes straight and sometimes curved slightly downward; color: Fern Green, Plate 0862/1. Hairs—none.

*New shoots.*—Dull. Color—Lettuce Green, Plate 861/3, heavily overlaid with Oxblood Red, Plate 00823/3. Prickles—several; color: near Oxblood Red, Plate 00823/3 at base, with points Fern Green, Plate 0862/3. Hairs—none.

I claim:

A new and distinct variety of rose plant of the hybrid tea class, substantially as herein shown and described, characterized particularly as to novelty by the unique combination of exceptional vigor and considerably greater than average plant height, flowers of good form, with the flower buds being long-pointed and having the habit of opening slowly into flowers of good longevity, a habit of bearing the flowers usually individually but always on stems of good length and good rigidity regardless of whether borne singly or on main canes of candelabra-cluster type, and a distinctive and attractive general color tonality of the flowers in the newly opened stage corresponding to Neyron Rose, said color changing to Tyrian Rose as the flowers age.

No references cited.